(12) United States Patent
Boyer et al.

(10) Patent No.: US 11,730,099 B2
(45) Date of Patent: Aug. 22, 2023

(54) COMPOSITIONS AND METHODS FOR LIQUID-MEDIATED DELIVERY OF POLLEN

(71) Applicant: Monsanto Technology LLC, St. Louis, MO (US)

(72) Inventors: Zachary Boyer, Fenton, MO (US); David A. Morgenstern, Creve Coeur, MO (US); Michelle R. Naert, Chesterfield, MO (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

(21) Appl. No.: 17/219,798

(22) Filed: Mar. 31, 2021

(65) Prior Publication Data

US 2021/0307273 A1    Oct. 7, 2021

Related U.S. Application Data

(60) Provisional application No. 63/158,325, filed on Mar. 8, 2021, provisional application No. 63/005,260, filed on Apr. 4, 2020.

(51) Int. Cl.
*A01H 1/02*    (2006.01)

(52) U.S. Cl.
CPC ............. *A01H 1/026* (2021.01); *A01H 1/024* (2021.01)

(58) Field of Classification Search
CPC ........... A01H 1/02; A01H 1/026; A01H 1/027
See application file for complete search history.

(56) References Cited

U.S. PATENT DOCUMENTS

| | | | |
|---|---|---|---|
| 6,723,680 | B2 | 4/2004 | Chung et al. |
| 10,076,091 | B2 | 9/2018 | Brown |
| 2013/0118067 | A1 | 5/2013 | Cope et al. |
| 2014/0289909 | A1 | 9/2014 | Byrum et al. |
| 2015/0257345 | A1* | 9/2015 | Brown ................... A01H 1/025 |
| 2017/0042102 | A1 | 2/2017 | Safreno |
| 2017/0238535 | A1 | 8/2017 | Cope et al. |
| 2018/0177752 | A1 | 6/2018 | Heller et al. |
| 2020/0296954 | A1 | 9/2020 | Cope et al. |
| 2021/0092920 | A1 | 4/2021 | Larue et al. |
| 2022/0279778 | A1 | 9/2022 | Boyer et al. |
| 2022/0338432 | A1 | 10/2022 | Larue et al. |
| 2022/0400637 | A1 | 12/2022 | Borrowman et al. |

FOREIGN PATENT DOCUMENTS

| | | |
|---|---|---|
| CN | 102599046 | 7/2012 |
| CN | 104719128 | 6/2015 |
| CN | 109105250 | 1/2019 |
| CN | 210202815 | 3/2020 |
| CN | 212184594 | 12/2020 |
| EP | 1785032 | 5/2007 |
| KR | 20050078007 | 8/2005 |
| WO | 2017180849 | 10/2017 |
| WO | 202055647 | 3/2020 |

OTHER PUBLICATIONS

Coe. Proc. Mo. Acad. Sci. 3: 7-8 (Abstract) (Year: 1966).*
U.S. Appl. No. 17/680,781, filed Feb. 25, 2022, Boyer et al.
U.S. Appl. No. 17/680,791, filed Feb. 25, 2022, Borrowman et al.
U.S. Appl. No. 17/762,658, filed Mar. 22, 2022, Larue et al.
Ali et al., Identification of potent gametocides for selective induction of male sterility in rice, Indian Journal of Genetics 59(4): 429-436, 1999.
Bosch et al., Pectin methylesterase, a regulator of pollen tube growth, Plant Physiology, 138: 1334-1346, 2005.
Clough and Bent, Floral dip: a simplified method for Agrobacterium-mediated transformation of *Arabidopsis thaliana*, Plant Journal 16(6): 735-743, 1998.
Diaz and Garay, Simple methods for in vitro pollen germination and pollen preservation of selected species of the genus, Agave, e-Gnosis, 6(2): 1-7, 2008.
Hopping and Jerram, Supplementary pollination of fruit trees. I. Development of suspension media. NZ J. Agri. Res. 23: 509-515, 1980.
Hopping and Simpson, Supplementary pollination of fruit trees. II. Suspension media for kiwifruit pollen, NZ J. Agri. Res. 25: 245-250, 1982.
International Search Report and Written Opinion regarding PCT Application No. PCT/US2019/054076, dated Dec. 30, 2019.
Jain and Shivanna, Storage of pollen grains of Crotmaria Retusa in oils, Sexual Plant Reproduction 3: 225-227, 1990.
Jayaprakash, Pollen germination in vitro, Pollination in Plants, Webpage [online], p. 81-96, 2018.
Johnson and Benard, Soybean genetics and breeding, Advances in Agronomy 14:149-221, 1962.
Loguercio, Pollen treatment in high osmotic potential: a simple tool for in vitro preservation and manipulation of viability in gametophytic populations, Brazilian Journal of Plant Physiology 14(1): 65-70, 2002.
Mishra and Shivanna, Efficacy of organic solvents for storing pollen grains of some leguminous taxa, Euphytica 31: 991-995, 1982.
Palmer et al., Pollen production in soybeans with respect to genotype, environment, and stamen position, Euphytica 27: 427-433, 1978.
Peterson et al., A flower and pod staging system for soybean, Annals of Botany 69: 59-67, 1992.
Pierce Biotechnology Inc., Protein stability and storage, Technical Resourse, 2005.

(Continued)

*Primary Examiner* — Keith O. Robinson
(74) *Attorney, Agent, or Firm* — Dentons Us LLP; Matthew Madsen; Christopher Luzecky

(57) ABSTRACT

The invention provides novel compositions and methods for liquid-mediated delivery of pollen to a female reproductive part of a recipient plant. The pollen suspension solutions provided include a surfactant, an oil, a solute, or an aqueous solution, and about 2% to about 20% pollen by weight. The methods provided include producing a liquid pollen suspension solution comprising pollen from a donor plant and spraying the solution onto at least a first female reproductive part of a recipient plant, thereby pollinating the female reproductive part with the pollen from the donor plant.

32 Claims, No Drawings

(56) References Cited

OTHER PUBLICATIONS

Talukdar and Shivakumar, Pollination without emasculation: an efficient method of hybridization in soybean (*Glycine max* (L.) *Merrill*), Current Science 103(6): 628-630, 2012.
Sadamori et al., Studies on the commercial hand pollination methods of apple flowers. I. Examination of pollen dilutes, of degree of pollen dilution and of pollinating methods. Bull. Tohoku Natl. Agric. Exp. Stn. 14:74-81, 1958.
Wood et al., Flight of the Robobees, Scientific American, 2013.
Yang et al, Ovary-drip transformation: a simple method for directly generating vector- and marker-free transgenic maize (*Zea mays* L.) with a linear GFP cassette transformation, Planta 229:793-801, 2009.
Yano et al., The use of liquid pollen extender thickened with polysaccharides for artificial pollination of kiwifruit, Acta Horticulturae 753: 415-424, 2007.
Zhao et al., Pollen magnetofection for genetic modification with magnetic nanoparticles as gene carriers, Nature Plants 3:956-964, 2017.
Hopping and Jerram, Supplementary pollination of tree fruits. II. Field trials on kiwifruit and Japanese plums. NZ J. Agri. Res. 23:517-521, 1980.
Broglia and Brunori, Synergistic effect of low temperature and high sucrose concentration on maize pollen viability in aqueous medium, Crop Sci., 34:528-9, 1994.
Coe, Liquid media suitable for suspending maize pollen before pollination (abstract), Proceedings of the Missouri Academy of Science 3:7, 1966.
Crespel and Mouchotte, Methods of cross-breeding, Reference Module in Life Sciences, 2016.
Graybosch and Palmer, Male sterility in soybean—an overview, American Journal of Botany 75(1): 144-456, 1988.
International Search Report and Written Opinion regarding International App. No. PCT/US21/25357, dated Aug. 11, 2021.
Pfahler, In vitro germination and pollen tube growth of maize (*Zea mays* L.) pollen. I. calcium and boron effects, Canadian Journal of Botany 45(6):839-845, 1967.
Sakamoto et al., Spray pollination as a labor-saving pollination system in Japanese pear (*Pyrus pyrifolia* (Burm.f.) Nakai): development of the suspension medium, Scientia Horitculturae 119:280-285, 2009.
Walker et al., Comparison of emasculation and non-emasculation for hybridization in soybean, Crop Science 19:285-286, 1979.
Xi et al. Induction of 2n pollen by colchicine in Populus x popularis and its triploid breeding, Sciendo 60:155-160, 2010.
Zeraatkar et al., Preliminary evaluation of artificial pollination in pistachio using pollen suspension spray, Plant Knowledge Journal 2(3): 94-98, 2013.
Erickson Variability of floral characteristics influences honey bee visitation to soybean blossoms, Crop Science 15:767-771, 1975.
Automatic & Air Atomizing Spray Nozzles. Spraying Systems Co. p. 78, (2018).
Ching. Controlled Pollination of Douglas fir: a Pictorial Manual on Technique, Forest Lands Research, Oregon Forest Research Center, Corvalis, 1960.
International Search Report and Written Opinion regarding International Application No. PCT/US22/18641, dated May 23, 2022.
Pacini, et al. Pollen Developmental Arrest: Maintaining Pollen Fertility in a World With a Changing Climate. Front. Plant Sci., May 24, 2019.
Rauf, et al. Advances in Plant Breeding Strategies: Agronomic, Abiotic and Biotic Stress Traits. Springer, Cham. 2016.
U.S. Appl. No. 18/179,970, filed Mar. 7, 2023, Larue, et al.

* cited by examiner

COMPOSITIONS AND METHODS FOR LIQUID-MEDIATED DELIVERY OF POLLEN

CROSS-REFERENCE TO RELATED APPLICATIONS

This application claims the priority of U.S. Provisional Appl. Ser. No. 63/005,260, filed Apr. 4, 2020, and U.S. Provisional Appl. Ser. No. 63/158,325, filed Mar. 8, 2021, the entire disclosure of each of which is incorporated herein by reference.

FIELD OF THE INVENTION

The present disclosure relates to the field of agricultural biotechnology, and more specifically to compositions and methods for improving pollination efficiency via liquid-mediated delivery of donor plant pollen grains to a female reproductive part of a recipient plant.

BACKGROUND OF THE INVENTION

Cross-pollination is used in plant breeding to introduce hybrid vigor, new traits, and novel phenotypes, and is used as the first step in the breeding cycle for many crop plants. Conventional methods for cross-pollination in many crop species, such as corn (*Zea mays*, also known as maize), involves conventional pollination, which includes selective detasseling of female plants and interspersing rows of the male parent line in a field of the female parent line. This process is inefficient as it depends on the effective flow of pollen to the female plants, which is vulnerable to wind and other variables, and requires that the male and female plants enter the reproductive phase at the same time. In addition, selective detasseling of female plants is time consuming and labor-intensive, and male plants occupy field space but do not produce hybrid seed. Typical commercial breeding programs require thousands or even millions of crosses such as, development crosses, backcrosses, and crosses for trait integration. As breeders aim to accelerate crop variety development and reduce labor needs, it is critical to develop pollination methods that improve efficiency. Hybrid seed production, in particular, would greatly benefit from production methods that use fields consisting mostly or entirely of female plants.

SUMMARY

In one aspect, a pollen suspension solution is provided herein comprising: a) a surfactant; b) an oil or an aqueous solution; and c) about 2% to about 20% pollen by weight. In some embodiments, the pollen suspension solution comprises about 2%, 4%, 6%, 8%, 10%, 12%, 14% 16%, 18% or about 20% pollen by weight, including all ranges derivable therebetween. In one embodiment, the pollen suspension solution comprises an oil and an aqueous solution, and in another embodiment, the pollen suspension solution is defined as a aqueous solution. In still other embodiments, the pollen suspension solution comprises less than about 5.0% surfactant by weight, less than about 4.0% surfactant by weight, less than about 3.0% surfactant by weight, less than about 2.0% surfactant by weight, less than about 1.0%, less than about 0.5%, or less than about 0.25% surfactant by weight, including all ranges derivable therebetween. Non-limiting examples of surfactants include a surfactant polymer, a modified cellulose polymer, a block copolymer of ethylene oxide and propylene oxide, a block copolymer of ethylene oxide and propylene oxide comprising a terminal alkyl group, and an agronomically acceptable dispersant polymer soluble in the pollen suspension solution. In other embodiments, the pollen suspension solution comprises an oil selected from the group consisting of a paraffin, an isoparaffin, and a silicon oil. In one embodiment, the solution further comprises at least one solute at a concentration of about 0.5M to about 3.0M to increase the tonicity of the solution, wherein the solute is impermeable to the pollen in the solution.

In another aspect, a pollen suspension solution is provided herein comprising at least one solute at a concentration of about 0.5M to about 3.0M to increase the tonicity of the solution, wherein the solute is impermeable to the pollen in the solution. In one embodiment, the solute is further defined as a monosaccharide, a disaccharide, a polysaccharide, a polyhydric alcohol, or a polyethylene glycol solute. Non-limiting examples of solutes include glucose, fructose, galactose, sucrose, lactose, maltose rehalose, cellobiose, chitobiose, kojibiose, nigerose, isomaltose, trehalose, sophorose, laminaribiose, gentiobiose, trehalulose, turanose, maltulose, leucrose, isomaltulose, gentiobiulose, mannobiose, melibiose, melibiulose, rutinose, rutinulose, xylobiose, maltotriose, melezitose, nigerotriose, maltotriulose, raffinose, kestose, maltodextrin, starch, glycogen, galactogen, cellulose, chitin, pectin, peptidoglycan, mannitol, sorbitol, xylitol, lactitol, isomalt, maltitol, sodium chloride, polyethylene glycol, and glycerol ethoxylate. In another embodiment, the solute is present in the solution at a) a concentration of between about 0.5M and about 3.0M; or b) about 5% to about 50% solute (weight/volume). In yet another embodiment, the pollen suspension solution is defined as an aqueous solution. In still yet another embodiment, the pollen suspension solution is defined as an isotonic solution.

In yet another aspect, the present disclosure provides a method for liquid-mediated delivery of pollen to a female reproductive part of a recipient monocot plant comprising the steps of: a) obtaining a liquid pollen suspension solution comprising pollen from a donor monocot plant as described herein; and b) spraying the pollen suspension solution onto at least a first female reproductive part of the recipient monocot plant, thereby pollinating the female reproductive part with the pollen from the donor monocot plant. In some embodiments, the recipient monocot plant is a corn plant, a wheat plant, or a rice plant. In further embodiments, the method comprises repeating steps a) and b) on two, three or more consecutive days. In particular embodiments, the recipient monocot plant can be rendered male sterile at the time of pollinating, including but not limited to, by the recipient plant being genetically male sterile, by being treated with a gametocide or by being manually emasculated, wherein the male reproductive parts or parts thereof of the recipient monocot plant are removed. In some embodiments, the method is defined as resulting in pollinating the female reproductive part with the pollen from the donor monocot plant such that a substantially equivalent number of seeds is produced compared to the number of seeds produced using a conventional pollination technique. In some embodiments, spraying the pollen suspension solution onto at least a first female reproductive part of the recipient monocot plant comprises air-assisted spraying. In particular embodiments, air-assisted spraying produces droplets with a volume weighted mean droplet diameter of less than about 300 µM, less than about 250 µM, less than about 200 µM, less than about 175 µM, less than about 150 µM or less than about 125 µM. In further embodiments, liquid cannot be visually observed at a distance of about 36 inches from the female reproductive part of the recipient monocot plant following the spraying. The methods of the invention may further include collecting seed resulting from pollination, and may in further embodiments comprise growing a progeny plant grown from the seed that is crossed with itself or a second plant. In some embodiments, the liquid pollen suspension solution is produced by a method comprising agitation of the solution. Non-limiting examples of agitation include vortexing or sparging of the pollen suspension solution.

In still yet another aspect, a method is provided for liquid-mediated delivery of pollen to a female reproductive part of a plant comprising the steps of: a) obtaining a pollen suspension solution as described herein that comprises a surfactant, an oil or an aqueous solution, and about 2% to about 20% pollen by weight; and b) spraying the pollen suspension solution onto at least a first female reproductive part of any recipient plant, thereby pollinating the female reproductive part with the pollen from the donor plant.

In one aspect, a method is provided herein for liquid-mediated delivery of pollen to a female reproductive part of a recipient plant comprising the steps of: a) obtaining a pollen suspension solution comprising at least one solute at a concentration of about 0.5M to about 3.0M to increase the tonicity of the solution, wherein the solute is impermeable to the pollen in the solution; and b) spraying the pollen suspension solution onto at least a first female reproductive part of a recipient plant, thereby pollinating the female reproductive part with the pollen from the donor plant. In one embodiment, the solute is further defined as a monosaccharide, a disaccharide, a polysaccharide, a polyhydric alcohol, or a polyethylene glycol solute. In another embodiment, the liquid pollen suspension solution is produced less than about 6 hours prior to the spraying. In still yet another embodiment, the liquid pollen solution is produced less than about 30 minutes to the spraying.

In another aspect, a method of producing hybrid seed of a monocot plant is provided comprising the steps of: a) producing a pollen suspension solution as described herein comprising a liquid solution and pollen from a donor monocot plant; b) spraying the pollen suspension solution onto a female reproductive part of a recipient monocot plant, thereby pollinating the female reproductive part with the pollen from the donor monocot plant; c) harvesting seed produced from the pollination; and d) identifying hybrid progeny. In some embodiments, the method further comprises repeating steps a) and b) on two or more consecutive days.

DETAILED DESCRIPTION

Modern plant breeding relies on outcrossing or cross-pollination to generate progeny plants having specific heritable traits that are obtained from each parental line. Therefore, throughput and efficiency play an important role in Fi population development and trait integration workflow efficiency. Corn (*Zea mays*), rice (*Oryza sativa*), and wheat (*Triticum aestivum*), which belong to the Poaceae family and the Liliopsida class (monocots) of plants, are examples of economically important agricultural crops in which breeding has been hampered by low efficiency procedures in controlled cross-pollination. Conventional methods for cross pollination of crop species such as corn entails emasculation of female plants and interspersing rows of male parent plants. This process is inefficient as it depends on the effective flow of pollen to the female plants, which is vulnerable to wind and other variables, and requires that the male and female plants enter the reproductive phase at the same time. In addition, male plants occupy field space but do not produce hybrid seed.

The invention represents a significant advance in the art in that it permits mechanical application of pollen to an all-female field, eliminating the need for in-field synchronized male and female plant development, and minimizing the effects of weather conditions. Application of monocot pollen at the scale required for hybrid seed production has previously been unfeasible. Monocot pollen clumps within hours of collection and it is difficult to effectively spray powder pollen. Furthermore, monocot pollen rapidly becomes nonviable in water and when exposed to typical ambient environmental conditions. The current invention surprisingly overcomes limitations in the art by permitting cross-pollination using liquid-mediated delivery of pollen to a female reproductive part of a recipient monocot plant, resulting in more efficient field use, eliminating the need for in-field synchronized male and female plant development, and minimizing the effects of variable weather conditions.

The present disclosure therefore permits implementation of high-throughput methods for the delivery of donor pollen to a recipient female reproductive part of a monocot plant. The methods provided herein substantially reduce the time and labor previously required to facilitate cross-pollination in monocot plants. This is of particular significance as modern plant breeding programs may require thousands or even millions of individual crosses on a yearly basis in order to produce a new plant variety with improved traits.

Liquid Pollination Solution Formulations

In one aspect, the present invention provides a pollen suspension solution comprising a surfactant, an oil or an aqueous solution, and about 2% to about 20% pollen by weight. The term "about" is used to indicate that a value includes the standard deviation of the mean for the device or method being employed to determine the value. As used herein, "pollen" refers to at least one pollen grain and may comprise a plurality of pollen grains. Non-limiting examples of pollen that may be used according to the compositions and methods of the invention include pollen collected from a dicot plant, a monocot plant, a Poaeceae family plant, a corn plant, a rice plant, or a wheat plant. In general, it will be desirable to use a solution containing components that facilitate uniform pollen dispersal and maintain high viability of pollen in solution. In some embodiments, the liquid pollen suspension solution comprises about 2% to about 20% pollen by weight. In some embodiments, the liquid pollen suspension solution comprises about 2% to about 15% pollen by weight. In some embodiments, the pollen suspension solutions comprises about 0.5%, 1%, 1.5%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, or 25% pollen by weight. Pollen for use in the present invention may be obtained or stored using any manual or automated methods well known in the art. In certain embodiments, pollen may be fresh, or may be dried or partially dried, prior to being added to the solution.

Non-limiting examples of components that may be used in the production of such a solution are provided herein and may include, in certain embodiments, an aqueous solution, an oil, a surfactant, an organic solvent, or a solute at a concentration of about 0.5M to about 3.0M to increase the tonicity of the solution, wherein the solute is impermeable to the pollen in the solution. In some embodiments, the solution may be an aqueous solution or may be comprised in other solvents. In some embodiments, the solution may comprise an oil and an aqueous solution. In some embodiments, the solution may comprise an oil, which serves to facilitate long term cold storage and viability of the pollen. Embodiments of the invention may comprise any oil known in the art, including for example a paraffin, an isoparaffin, or a silicone oil, or any combination thereof. In some embodiments, the solution may comprise a synthetic solvent, for example Isopar M™, which may be in the solution at a concentration of about 48% to about 100% Isopar M™ by weight. In some embodiments, the solution may comprise a monosaccharide, a disaccharide, a polysaccharide, a polyhydric alcohol, or a polyethylene glycol solute.

In some embodiments, the solution may comprise a surfactant, which serves to uniformly disperse pollen in the solution. Embodiments of the invention may comprise any surfactant, or combination of surfactants, known in the art, for example modified cellulose polymer, a block copolymer of ethylene oxide and propylene oxide, or an agronomically acceptable dispersant polymer. In certain embodiments, the surfactant may be a block copolymer of ethylene oxide and propylene oxide further comprising a terminal alkyl group. In some embodiments, the surfactant may be one or more of Atlox™ LP-1, Lutensol® XL-80, Pluronic® P104, Walocel™ C CRT30, Poly Suga® Mulse, Mazol 300K, BREAK THRU® DA 647, TOXIMUL® 8325, Atlas G-5000, METHOCEL™ F50, Surfynol®, METHOCEL™ E19, BREAK THRU® DA 675, Atlox™ 4915, TOXIMUL® 8320, or TOXIMUL® 8242, and may, as for example, be in the solution at a concentration of less than about 5.0%, less than about 4.0%, less than about 3.0%, less than about 2.0%, less than about 1.0%, or less than about 0.5% surfactant by weight. In specific embodiments, the surfactant may be in the solution at a concentration of less than about 5.0%, 4.5%, 4.0%, 3.5%, 3.0%, 2.5%, 2.0%, 1.5%, 1.0%, 0.9%, 0.8%, 0.7%, 0.6% 0.5%, 0.4%, 0.3%, 0.2%, or 0.1% surfactant by weight, including all ranges derivable therebetween.

In some embodiments, the solution may comprise at least one solute at a concentration of about 0.5M to about 3.0M to increase the tonicity of the solution, wherein the solute is impermeable to the pollen in the solution, which serves to prevent pollen lysis in aqueous solutions. In one embodiment, sufficiently high concentrations of solute may also inhibit precocious germination. "Tonicity" as used herein is influenced by solutes that cannot cross the membrane. Solutes that are able to freely cross the membrane do not influence tonicity because they equilibrate across the membrane without net solvent movement. As used herein the term "impermeable" refers to a state where an isotonic solution of the solute when first mixed with pollen produces less than about 10% pollen lysis over the first 4 hours that the pollen is in contact with the solution. As used herein the term "isotonic" refers to a state where the osmolarity of the extracellular solution is equal to the osmolarity of the pollen cytoplasmic space. In a particular embodiment, a pollen suspension solution comprising at least one solute of the present invention is isotonic with corn pollen at a concentration of about 1.5M. The isotonic concentration may vary for different crop species and can be determined empirically using methods known in the art and provided herein. Suitable solutes for use in a pollen suspension solution of the present invention may be identified empirically using the methods described herein. It may be desired for example to utilize a solute which is impermeable to the pollen and maintains pollen viability and fertility. Pollen viability and fertility may in one example be evaluated using an in vitro germination assay, which is routine in the art.

In some embodiments, the solute according to the invention is present in the solution at a) a concentration of between about 0.5M and about 3.0M; or b) about 5% to about 50% solute (weight/volume). Weight/volume as used herein is used to refer to the weight of the solute/volume of solution. The solute may be present in the solution, for example, at a concentration of about 0.5M, 1.0M, 1.5M, 2.0M, 2.5M, or 3.0M, including all ranges derivable therebetween. The solute may be present for example at about 5%, 10%, 15%, 20%, 25%, 30%, 35%, 40%, 45%, or 50% solute (weight/volume), including all ranges derivable therebetween. Non-limiting examples of solutes that may be used in the production of such a liquid pollen suspension solution include a monosaccharide solute, a disaccharide solute, a polysaccharide solute, a polyhydric alcohol solute, a polyethylene glycol solute, glucose, fructose, galactose, sucrose, lactose, maltose rehalose, cellobiose, chitobiose, kojibiose, nigerose, isomaltose, trehalose, sophorose, laminaribiose, gentiobiose, trehalulose, turanose, maltulose, leucrose, isomaltulose, gentiobiulose, mannobiose, melibiose, melibiulose, rutinose, rutinulose, xylobiose, maltotriose, melezitose, nigerotriose, maltotriulose, raffinose, kestose, maltodextrin, starch, glycogen, galactogen, cellulose, chitin, pectin, peptidoglycan, mannitol, sorbitol, xylitol, lactitol, isomalt, maltitol, sodium chloride, polyethylene glycol, and glycerol ethoxylate. For aqueous phases containing solutes to increase tonicity, particularly sugars and sugar alcohols, the addition of non-phytotoxic biocides may be used in one embodiment to reduce the risk of microbial growth during storage. Non-phytotoxic biocides are well-known in the art, non-limiting examples of which include sodium sulfite, potassium sulfite, potassium sorbate, sodium benzoate, and potassium benzoate. The solution may comprise for example about 0.1% sodium sulfite or potassium sulfite, about 0.1% potassium sorbate, about 0.05% to about 0.1% sodium benzoate or potassium benzoate, or any combinations thereof. In one example, the pollen suspension solution may comprise more than one solute, each of which is capable of increasing the tonicity of the liquid pollen suspension solution at a concentration between about 0.5M and about 3.0M. The pollen suspension solution may comprise for example at least 1 solute, at least 2 different solutes, at least 3 different solutes, or at least different 4 solutes. In one embodiment, the total concentration of the at least 2 different solutes, at least 3 different solutes, or at least 4 different solutes is between about 0.5M and about 3.0M. In another embodiment the at least 2 different solutes, at least 3 different solutes, or at least different 4 solutes are present in the pollen suspension solution at about 5% to about 50% total solute (weight/volume).

In certain embodiments, the pollen suspension solution may comprise one or more buffering agents. Buffering agents may be used for example to keep the pH of the solution within a desired range. Potentially any buffering agent known in the art could find use in accordance with the present invention, non-limiting examples of which include citric acid, acetic acid, potassium dihydrogen phosphate, N-cyclohexyl-2-aminoethanesulfonic acid, borate, tris(hydroxymethyl)methylamino]propanesulfonic acid (TAPS), 2-(bis(2-hydroxyethyl)amino)acetic acid (Bicine), tris(hydroxymethyl)aminomethane (Tris), N-[tris(hydroxymethyl) methyl]glycine (Tricine), 3-[N-tris(hydroxymethyl)methylamino]-2-hydroxypropanesulfonic acid (TAPSO), 4-(2-hydroxyethyl)-1-piperazineethanesulfonic acid (HEPES), 2-[[1,3-dihydroxy-2-(hydroxymethyl)propan-2-yl]amino] ethanesulfonic acid (TES), 3-(N-morpholino)propanesulfonic acid (MOPS), piperazine-N,N'-bis(2-ethanesulfonic acid) (PIPES), 2-(N-morpholino)ethanesulfonic acid (MES). In specific embodiments, the buffering agent may be present in the solution at a concentration of about 0.03% to about 3.0% buffering agent by weight. The buffering agent may be present for example at a concentration of about 0.03%, 0.05%, 0.07%, 0.1%, 0.2%, 0.4%, 0.6%, 0.8%, 1.0%, 1.5%, 2.0%, 2.5%, or 3.0%, buffering agent by weight.

Delivery of Pollen Solution for Pollination of Plants

The present invention surprisingly permits cross-pollination of potentially any flowering plant or grass. In one aspect, the method includes producing a liquid pollen suspension comprising pollen from a donor monocot plant and spraying the suspension onto a female reproductive part of a recipient monocot plant, thereby pollinating the female reproductive part with the pollen from the donor plant. As used herein the term "spraying" refers to generating droplets of a pollen suspension solution of a size capable of delivering the pollen to female reproductive portions of a recipient plant, thereby pollinating the recipient plant. Non-limiting examples of spraying comprise generating droplets with a volume weighted mean droplet diameter of less than about 300 μM, less than about 250 μM, less than about 200 μM, less than about 175 μM, less than about 150 μM or less than about 125 μM. Suitable sprays can be produced with common agricultural nozzles rated for "Fine" or "Very Fine" sprays or by using air-assisted spraying, as further described below.

In some embodiments, the optimum components for use in the liquid pollen suspension solution may be optimized for a particular application. Such parameters can be determined empirically using the methodology described herein. To promote cross-pollination, for example, it may be desired to use a pollen suspension solution containing components that facilitate uniform pollen dispersal, maintain high viability of the pollen grains, and which do not significantly hinder fertilization and seed development when sprayed onto the female reproductive part of a recipient monocot plant. Examples of such components include, but are not limited to, Atlox™ LP1, Isopar M, Harborlite, Lutensol® XL-80, Pluronic® P104, Walocel C CRT30, Poly Suga® Mulse, Mazol 300K, BREAK THRU® DA 647, TOXIMUL® 8325, Atlas G5000, METHOCEL™ F50, Surfynol®, METHOCEL™ E19, Break-thru DA 675, Atlox™ 4915, TOXIMUL® 8320, and TOXIMUL® 8242, a monosaccharide solute, a disaccharide solute, a polysaccharide solute, a polyhydric alcohol solute, a polyethylene glycol solute, glucose, fructose, galactose, sucrose, lactose, maltose rehalose, cellobiose, chitobiose, kojibiose, nigerose, isomaltose, trehalose, sophorose, laminaribiose, gentiobiose, trehalulose, turanose, maltulose, leucrose, isomaltulose, gentiobiulose, mannobiose, melibiose, melibiulose, rutinose, rutinulose, xylobiose, maltotriose, melezitose, nigerotriose, maltotriulose, raffinose, kestose, maltodextrin, starch, glycogen, galactogen, cellulose, chitin, pectin, peptidoglycan, mannitol, sorbitol, xylitol, lactitol, isomalt, maltitol, sodium chloride, polyethylene glycol, and glycerol ethoxylate. In some embodiments, the pollen suspension solvent may comprise Isopar M, which may be in the solution at a concentration of about 48% to about 100% Isopar M by weight. In other embodiments, the solution may comprise a surfactant, which serves to uniformly disperse pollen in the solution. Examples of surfactants include Atlox™ LP-1, Lutensol® XL-80, Pluronic® P104, Walocel™ C CRT30, Poly Suga® Mulse, Mazol 300K, BREAK THRU® DA 647, TOXIMUL® 8325, Atlas G5000, METHOCEL™ F50, Surfynol®, METHOCEL™ E19, Break-thru DA 675, Atlox™ 4915, TOXIMUL® 8320, or TOXIMUL® 8242, and may, as one example, be in the solution at a concentration of less than about 5.0%, 4.0%, 3.0%, 2.0%, 1.0%, or 0.5% surfactant by weight.

In particular embodiments, the methods described herein may comprise repeating the steps of producing a liquid pollen suspension solution comprising pollen from a donor monocot plant, and spraying the solution onto at least a first female reproductive part of a recipient monocot plant, thereby pollinating the female reproductive part with the pollen from the donor plant on two or more consecutive days. In corn, for example, it was found that repeating the spraying steps on two or three consecutive days resulted in higher seed set compared to producing the liquid pollen suspension solution and spraying the solution onto at least a first female reproductive part of a recipient monocot plant on only one day (Table 12, Table 13, Table 14).

In still other embodiments, the methods described herein may comprise pollination of flowers that are male sterile at the time of pollinating. Depending upon the developmental stage of the plant, donor pollen applied for cross-pollination could compete with pollen produced by the recipient plant. In order to improve the efficacy of the cross-pollination, it may be advantageous in some cases that the recipient plant be male sterile in an effort to reduce competition with selfing. Thus, a male sterility system could be employed with the female parent plant in a particular cross. Many such male sterility systems are well known, including cytoplasmic male sterility (CMS) and genic male sterility (GMS). CMS and GMS facilitate hybrid seed production for many crops and thus allow breeders to harness yield gains associated with hybrid vigor. The use of a gametocide presents an alternative method to produce male sterility. Gametocides affect processes or cells involved in the development, maturation or release of pollen. Plants treated with such gametocides are rendered male sterile, but typically remain female fertile. The use of chemical gametocides is described, for example, in U.S. Pat. No. 4,936,904, the disclosure of which is specifically incorporated herein by reference in its entirety. Furthermore, the use of Roundup herbicide in combination with glyphosate tolerant corn plants to produce male sterile corn plants is disclosed in PCT Publication WO 98/44140. Several gametocides have been reported effective in inducing pollen sterility in various crops and are well known in the art. Such gametocides include sodium methyl arsenate, 2,3-dichloroisobutyrate, sodium 2,2-dichloropropionate, gibberellic acid, maleic hydrazide (1,2-dihydropyridazine, 3-6-dione), 2,4-dichloro phenoxy acetic acid, ethyl 4-fluorooxanilate, trihalogenated methylsulfonamides, ethyl and methyl arsenates (Ali et al., 1999). Physical emasculation of the recipient monocot plant presents another alternative to produce male sterility. Following emasculation, the plants are then typically allowed to continue to grow and natural cross-pollination occurs as a result of the action of wind, which is normal in the pollination of grasses, including corn. As a result of the emasculation of the female parent plant, all the pollen from the male parent plant is available for pollination because the male reproductive portion, and thereby pollen bearing parts, have been previously removed from all plants of the plant being used as the female in the hybridization. Of course, during this hybridization procedure, the parental varieties are grown such that they are isolated from other plants to minimize or prevent any accidental contamination of pollen from foreign sources. These isolation techniques are well within the ability of those skilled in this art.

The methods described herein may include in specific instances the step of producing a liquid pollen suspension solution comprising pollen from a donor monocot, wherein the suspension solution is produced about 6 hours prior, about 5 hours prior, about 4 hours prior, about 3 hours prior, about 2 hours prior, about 1 hour prior, about 30 minutes prior, about 25 minutes prior, about 20 minutes prior, about 15 minutes prior, about 10 minutes prior, about 5 minutes prior, about 1 minute prior, or about 30 seconds prior to spraying the solution. In corn, for example, it was found that surprisingly pollen does not lyse when briefly fluidized in water but instead produces a seed set comparable to that produced using conventional pollination techniques (Table 8, Table 12, and Table 14).

The methods provided herein may include in specific embodiments, a step of diluting a produced pollen suspension solution prior to spraying. As a non-limiting example, a produced pollen suspension solution comprising from about 10% to about 50% (weight/volume) of a solute according to the present invention may be diluted to produce a diluted solution comprising from about 5% to about 25% solute (weight/volume) prior to spraying. The produced pollen suspension solution may comprise for example, about 10%, 15%, 20%, 25%, 30%, 35%, 40%, 45%, or 50% solute (weight/volume). The diluted pollen suspension solution may comprise for example, about 5%, 10%, 15%, 20%, or 25% solute (weight/volume). The produced pollen suspension solution may be produced about 6 hours prior, about 5 hours prior, about 4 hours prior, about 3 hours prior, about 2 hours prior, about 1 hour prior, about 30 minutes prior, about 25 minutes prior, about 20 minutes prior, about 15 minutes prior, about 10 minutes prior, about 5 minutes prior, about 1 minute prior, or about 30 seconds prior to diluting the solution. The diluted pollen suspension solution may be made from the produced pollen suspension solution about 6 hours prior, about 5 hours prior, about 4 hours prior, about 3 hours prior, about 2 hours prior, about 1 hour prior, about 30 minutes prior, about 25 minutes prior, about 20 minutes prior, about 15 minutes prior, about 10 minutes prior, about 5 minutes prior, about 1 minute prior, or about 30 seconds prior to spraying the solution.

In particular embodiments, the methods described herein are carried out to produce a substantially equivalent number of seeds compared to the number of seeds produced using a conventional pollination technique. Substantial equivalence is evaluated by comparing seed sets produced using liquid-mediated pollen delivery to seed sets produced using one day hand pollination, where pollen from the same lot is applied to female plants from the same lot on the same day. As used herein, "substantially equivalent" refers to a characteristic wherein the mean value±standard deviation of the test population does not deviate more than about 20% from the mean value±standard deviation of the control population. In corn, it was found that the following pollen suspension solutions produce a substantially equivalent number of seeds compared to the number of seeds produced using a conventional pollination technique: 3.0% Atlox™ LP1 in Isopar M, pollen in water, 0.5% METHOCEL™ F50, and 0.2% TOXIMUL® 8320 (Table 4, Table 12, and Table 13), when liquid-mediated pollination is performed on two or three consecutive days during a period of silk receptivity.

The methods described herein may comprise spraying the pollen suspension solution using air-assisted spraying. In some embodiments, the spraying may produce droplets with a volume weighted mean droplet diameter of less than about 300 μM. In some embodiments, liquid may not be observed visually at a distance of about 36 inches from the female reproductive part of the recipient monocot plant following the air-assisted spraying. In other embodiments, the pollen suspension solution may be sprayed at a pressure of about 10 psi, about 20 psi, about 30 psi, or about 40 psi. As monocot pollen has a tendency to clump and lyse upon exposure to water, it may be beneficial to minimize the amount of aqueous pollen suspension solution applied to the female reproductive part of the recipient monocot plant.

The step of selecting a progeny seed or plant that results from pollinating with the pollen suspension solution may also be carried out. This could be facilitated by use of a polymorphic marker allele contained in the pollen donor that serves to identify progeny plants or seeds of that donor. Morphological markers or biochemical/protein markers have commonly been used as tools for selection of plants with desired traits in breeding. Molecular marker techniques that have been extensively used and are particularly promising for application to plant breeding include: restriction fragment length polymorphisms (RFLPs), amplified fragment length polymorphisms (AFLPs), random amplified polymorphic DNA (RAPD), microsatellites or simple sequence repeats (SSRs), and single nucleotide polymorphisms (SNPs) (Al-Khayri et al., 2016).

Methods of the present invention involving producing a liquid pollen suspension solution can include use of agitation of the pollen suspension solution. In some embodiments, the agitation may comprise low shear agitation, which may comprise introducing air bubbles into the pollen suspension solution. In particular embodiments, air bubbles may be introduced into the pollen suspension solution by vortexing or by sparging. As used herein, "vortexing" refers to contacting a rapidly oscillating device with a container comprising a liquid solution. As used herein, "sparging" refers to agitating a liquid by introducing air or gas through a tube.

In one aspect, a liquid pollen suspension solution comprising pollen from a donor plant and spraying the solution onto at least a first female reproductive part of a recipient plant, thereby pollinating the female reproductive part with the pollen from the donor plant, wherein the pollen suspension solution comprises a surfactant, an oil or an aqueous solution, and about 2% to about 20% pollen by weight. In some embodiments, beneficial components for a pollen suspension solution for use in the method, include, but are not limited to, Atlox™ LP1, Isopar M, Harborlite, Lutensol® XL-80, Pluronic® P104, Walocel™ C CRT30, Poly Suga® Mulse, Mazol 300K, BREAK THRU® DA 647, TOXIMUL® 8325, Atlas G5000, METHOCEL™ F50, Surfynol®, METHOCEL™ E19, Break-thru DA 675, Atlox™ 4915, TOXIMUL® 8320, and TOXIMUL® 8242. In some embodiments, the pollen suspension solution for use in the method may comprise Isopar M, which may be in the solution at a concentration of about 48% to about 100% Isopar M by weight.

In yet another aspect, a method of the present invention comprises producing a pollen suspension solution comprising a liquid and pollen from a donor monocot plant, spraying the solution onto a female reproductive part of a recipient monocot plant, thereby pollinating the female reproductive part with the pollen from the donor monocot plant. The method may also comprise harvesting seed produced from the pollination, and can include identifying hybrid progeny.

The methods disclosed herein may be implemented for improved cross-pollination of potentially any plants. Such plants can include, but are not limited to, members of the Poaceae family, non-limiting examples of which are corn, wheat, and rice.

Modified Plants and Seeds

One aspect of the invention provides selection of progeny plants and seeds that result from the methods described herein. In some embodiments, the progeny plants and seeds may be defined as comprising a detectable modification relative to the female parent plant. One method of producing such plants and seeds is through use of an allele produced by plant genetic transformation. Suitable methods for transformation of host plant cells for use with the current invention are well known in the art and include any method by which DNA can be introduced into a cell (for example, where a recombinant DNA construct is stably integrated into a plant chromosome) and are well known in the art. Some widely utilized methods for cell transformation are Agrobacterium-mediated transformation, microprojectile bombardment-mediated transformation, and cell penetrating peptide-mediated delivery of DNA modifying agents.

Another method of producing modified plants and seeds is through genome editing. As used herein, the term "genome editing" refers to the use of genome editing methods and a site-specific genome modification enzyme to modify a nucleotide sequence. In some embodiments, donor pollen may be transformed using techniques known in the art to contain one or more reagents that mediate genome-specific modification in a plant. Pollen grains may be used in accordance with the invention that comprise any such reagents of loci generated with use of such reagents at any current or prior generation.

Suitable methods for altering a wild-type DNA sequence at a pre-determined chromosomal site include any method known in the art. Targeted modification of plant genomes through the use of genome editing methods and reagents can be used to create improved plant lines through modification of plant genomic DNA. In addition, genome editing methods and reagents can facilitate targeted insertion of one or more nucleic acids of interest into a plant genome. Exemplary methods for introducing donor polynucleotides into a plant genome or modifying the genomic DNA of a plant include the use of genome editing reagents such as: sequence-specific recombinases, endonucleases, zinc-finger nucleases, engineered or native meganucleases, TALE-endonucleases, RNA-guided endonucleases (for example, a Clustered Regularly Interspersed Short Palindromic Repeat (CRISPR)/Cas9 system, a CRISPR/Cpf1 system, a CRISPR/CasX system, a CRISPR/CasY system, a CRISPR/Cascade system), and CRISPR-associated transposases (Strecker, et al., 2019) and (Klompe, et al. 2019). Several embodiments relate to methods of genome editing using single-stranded oligonucleotides to introduce precise base pair modifications in a plant genome, as described by Sauer et al. (*Plant Physiol.* 170 (4):1917-1928; 2016).

As used herein, the term "site-specific genome modification enzyme" refers to any enzyme that can modify a nucleotide sequence in a sequence-specific manner. In some embodiments, a site-specific genome modification enzyme modifies the genome by inducing a single-strand break. In some embodiments, a site-specific genome modification enzyme modifies the genome by inducing a double-strand break. In some embodiments, a site-specific genome modification enzyme comprises a cytidine deaminase. In some embodiments, a site-specific genome modification enzyme comprises an adenine deaminase. In the present disclosure, site-specific genome modification enzymes include endonucleases, recombinases, transposases, deaminases, helicases and any combination thereof. In some embodiments, the site-specific genome modification enzyme is a sequence-specific nuclease.

EXAMPLES

Example 1. Development of Solution for Delivery of Pollen

For liquid pollination of plants, pollen grains obtained from a donor plant can be mixed into a liquid solution to facilitate delivery to the female reproductive part of a recipient plant. The components and their concentrations in the pollen liquid solution are important to the efficacy of the solution, as they influence not only the pollen viability but also the success rate of hybrid seed production in pollinated plants. However, while efficiency can be improved by optimization of the components and concentrations in a given pollen suspension solution, numerous substitutions and modifications are possible while still achieving pollination as illustrated herein below in Table 1. Table 1 includes results produced using different methods of pollen suspension application conducted on different days with distinct female recipient plants. The results provided in Table 1 are, however, representative of the potential for certain liquid pollen suspensions to produce relatively high seed set compared to other liquid pollen suspensions, which are relatively unsuccessful.

TABLE 1

Exemplary liquid pollen suspension solutions and representative number of kernels produced following pollination using air-assisted spraying.

| Liquid Pollen Suspension Solution | No. Kernels Produced |
|---|---|
| IL3 (3.0% Atlox ™ LP1 in Isopar M) | 163 ± 65 |
| 0.5% Atlox ™ LP-1 in Isopar M | 42.7 ± 24.6 |
| 1.0% Atlox ™ LP-1 in Isopar M | 43.7 ± 2.9 |
| IL3 + 2% Walocel ™ C CRT30/1.0% Pluronic ® P104 (1:1) | 2.67 ± 3.09 |
| Isopar M | 6 ± 7 |
| 1.0% Pluronic ® P104 in IL-3 | 12 ± 2 |
| 0.5% BREAK THRU ® DA 647 in IL-3 | 14 ± 20 |
| 1.0% Poly Suga ®Mulse in IL-3 | 2.7 ± 1.5 |
| M3 oil (Mazol 300K 0.7%; Atlox ™ LP1 3.0%; Isopar M 96.3%) + 23% PEG1500/1.0% Pluronic ® P104 (1:1) | 25.67 ± 31.35 |
| M3 oil + 12% PEG1000/0.4% METHOCEL ™ F50/0.6% Pluronic ® P104 (1:1) | 3.67 ± 0.47 |
| M3 oil + 8% PEG1000/2.0% METHOCEL ™ E19/1.0% Pluronic ® P104 (1:1) | 12.67 ± 1.69 |
| Water | 295 ± 55 |
| 1.0% Lutensol ® XL-80 | 6 ± 2 |
| 1.0% Pluronic ® P104 | 47 ± 30 |
| 0.5% BREAK THRU ® DA 647 | 88 ± 21 |
| 0.5% Pluronic ® P104 | 76 ± 42 |
| 0.25% TOXIMUL ® 8325 | 73 ± 13 |
| 0.25% Atlas G5000 | 37 ± 28 |
| 0.5% METHOCEL ™ F50 | 200 ± 77 |
| 0.5% Surfynol ® | 2 ± 3 |
| 1.0% METHOCEL ™ E19 | 23 ± 15 |
| 0.5% Break-thru DA 675 | 32 ± 6 |
| 0.5% METHOCEL ™ E19 | 69 ± 11 |
| 0.2% Atlox ™ 4915 | 163 ± 4 |
| 0.2% TOXIMUL ® 8320 | 166 ± 34 |
| 0.2% TOXIMUL ® 8242 | 46 ± 31 |

Tests were performed to develop a liquid pollen suspension solution that promotes pollen singulation, maintains high pollen viability, and produces seed when sprayed on the female reproductive part of a recipient plant. A number of surfactants were tested for use in the liquid pollen suspension solution, including Atlox™ LP-1, Lutensol® XL-80, Pluronic® P104, Walocel™ C CRT30, Poly Suga®Mulse, Mazol 300K, BREAK THRU® DA 647, TOXIMUL® 8325, Atlas G5000, METHOCEL™ F50, Surfynol®, METHO- CEL™ E19, Break-thru DA 675, Atlox™ 4915, TOX-IMUL® 8320, and TOXIMUL® 8242. Liquid mediated delivery of pollen suspension solutions comprising 3.0% Atlox™ LP1, 0.2% Atlox™ 4915, 0.2% TOXIMUL® 8320, or 0.5% METHOCEL™ F50 produced seed sets comparable to those produced using conventional cross-pollination techniques (Table 1, Table 2, Table 13, and Table 14).

Based on the results obtained from experiments testing individual liquid pollen suspension solutions, it was determined that beneficial components for a solution for liquid-mediated pollen delivery include, but are not limited to, the following components: Atlox™ LP1, Isopar M, Harborlite, Lutensol® XL-80, Pluronic® P104, Walocel™ C CRT30, Poly Suga®Mulse, Mazol 300K, BREAK THRU® DA 647, TOXIMUL® 8325, Atlas G5000, METHOCEL™ F50, Surfynol®, METHOCEL™ E19, Break-thru DA 675, Atlox™ 4915, TOXIMUL® 8320, and TOXIMUL® 8242.

In certain embodiments, solutions and methods described herein may be used together with any plant. In specific embodiments, solutions and methods provided may be used together with crop plants, such as monocot crop plants. Non-limiting examples of crop plants that may be used together with the solutions and methods described herein include corn, wheat, barley, rice, and sorghum.

Example 2. Liquid-Mediated Pollen Delivery in Corn Plants Using Oil Based Solutions Liquid-mediated delivery of monocot pollen to a female reproductive part of a recipient monocot plant is challenging as monocot pollen has a tendency to clump and lyse upon exposure to water. A liquid-mediated delivery method was developed to overcome these challenges and to deliver monocot pollen to a female reproductive part of a recipient monocot plant with minimal water using oil based solutions.

A suitable liquid-mediated pollen delivery method was evaluated by examining seed set following pollination according to the following protocols: 1) 32 mg dry corn pollen, sprinkled; 2) 50 mg corn pollen in 300 mg IL3 (3.0% Atlox™ LP1 in Isopar M); 3) 50 mg corn pollen in 600 mg IL3; 4) 50 mg corn pollen in 300 mg M3 oil (Mazol 300K 0.7%; Atlox™ LP1 3.0%; Isopar M 96.3%)+300 mg 23% PEG1500/1.0% Pluronic® P104; 5) 50 mg corn pollen in 300 mg IL3+300 mg 2% Walocel™ C CRT30/1.0% Pluronic® P104. For the dry control, 32 mg of fresh pollen was weighed into vials that were kept cool until pollen was sprinkled onto the silks. For the other protocols, 50 mg of pollen was added to vials comprising the oil, which was pre-conditioned at 7° C., to make a pollen suspension solution. Pollen suspension solutions comprising oil or aqueous media were applied to ears using air-assisted spraying. The pollen suspension solutions were either vortexed and added immediately to the reservoir of a gravity-fed airbrush (Paasche TG-3F from Paasche Airbrush, Kenosha, Wis.), or combined with an aqueous solution, shaken, and poured into the airbrush reservoir. Pollen suspension solutions were promptly sprayed directly over the ear using the airbrush and a 0.66 m or 0.38 mm tip at 20-35 psi. All pollinations were completed within 2.5 hours of adding pollen to oil. Oil pollen suspension solutions without emulsification showed a clear improvement in seed set when using 600 mg rather than 300 mg of oil (Table 2). Emulsified pollen suspensions resulted in low seed set (Table 2).

TABLE 2

Seed set following airbrush application of oil-based pollen suspension solution with and without emulsification.

| Formulation | Ear 1 | Ear 2 | Ear 3 | Average |
|---|---|---|---|---|
| Dry, sprinkled | 209 | 317 | 372 | 299 ± 67.71 |
| 300 mg IL3 | 0 | 99 | N/A | 49.5 ± 49.5 |
| 600 mg IL3 | 98 | 228 | N/A | 163 ± 65 |
| M3/PEG1500 | 4 | 3 | 70 | 25.67 ± 31.35 |
| IL3/Walocel ™ | 0 | 1 | 7 | 2.67 ± 3.09 |

A suitable liquid-mediated pollen delivery method was evaluated by examining seed set following pollination according to one of the following protocols: 1) 32 mg dry corn pollen, sprinkled; 2) two applications of 50 mg pollen in 300 mg IL3, 30 minutes apart; 3) 50 mg pollen in 500 mg IL3; 4) 50 mg corn pollen in 300 mg IL3+300 mg 2% Walocel™ C CRT30/1.0% Pluronic® P104; 5) 50 mg corn pollen in 300 mg M3 oil+300 mg 12% PEG1000/0.4% METHOCEL™ F50/0.6% Pluronic® P104. For the dry control, 32 mg of fresh pollen was weighed into vials that were kept cool until pollen was sprinkled onto the silks. For the other protocols, 50 mg of pollen was added to vials comprising the oil, which was pre-conditioned at 7° C., to make a pollen suspension solution. The pollen suspension solutions were either vortexed and added immediately to the reservoir of a Paasche TG-3F gravity-fed airbrush or combined with an aqueous solution, shaken, and poured into the airbrush reservoir. Pollen suspension solutions were promptly sprayed over the ear using the airbrush and either a 0.66 mm tip (oils) or 0.38 mm tip (oil emulsions) at 30 psi. The 12% PEG1000+0.4% METHOCEL™ F50+0.6% Pluronic® P104 solution was prepared by bringing 35 g of water to a near boil on a stirring hotplate then added 400 mg of METHOCEL™ F50 with rapid stifling. A room temperature mixture of 1 g Pluronic® P104, 12 g PEG 1000, and 51.6 g of water was then added, followed by removal from heat and continued stirring for another 10 minutes. The protocol comprising two applications of oil pollen suspension solution showed reduced seed set compared to the single application protocol (Table 3). Protocols comprising emulsified pollen suspension solutions resulted in low seed set (Table 3).

TABLE 3

Seed set following airbrush application of oil-based pollen suspension solutions with varying oil levels.

| Formulation | Ear 1 | Ear 2 | Ear 3 | Average |
|---|---|---|---|---|
| Dry, sprinkled | 309 | 341 | 388 | 346 ± 32.4 |
| 300 mg IL3, 2X. | 44 | 61 | 48 | 51 ± 7.3 |
| 500 mg IL3 | 117 | 112 | 3 | 77.3 ± 52.6 |
| IL3/Walocel ™ | 3 | 3 | 0 | 2 ± 1.4 |
| M3/PEG1000/ METHOCEL ™ F50 | 4 | 4 | 3 | 3.67 ± 0.47 |

A suitable liquid-mediated pollen delivery method was evaluated by examining seed set following pollination according to one of the following protocols: 1) 32 mg dry corn pollen, sprinkled; 2) 50 mg pollen in 600 mg IL3; 3) 50 mg pollen in 300 mg M3 oil+300 mg 8% PEG1000/2.0% METHOCEL™ E19/1.0% Pluronic® P104. For the dry control, 32 mg of fresh pollen was weighed into vials that were kept cool until pollen was sprinkled onto the silks. For the other protocols, 50 mg of pollen was added to vials comprising the oil, which was pre-conditioned at 7° C., to make a pollen suspension solution. The pollen suspension solutions were either vortexed and added immediately to the reservoir of a Paasche TG-3F gravity-fed airbrush or combined with an aqueous solution, shaken, and poured into the airbrush reservoir. Pollen suspension solutions were promptly sprayed over the ear using the airbrush and either a 0.66 mm (oils) or 0.38 mm tip (oil emulsions) at 30 psi. The 8% PEG1000+2.0% METHOCEL™ E19+1.0% Pluronic® P104 solution was prepared by bringing 35 g of water to a near boil on a stifling hotplate then added 2.0 g of METHOCEL™ E19 with rapid stifling. A room temperature mixture of 1 g Pluronic® P104, 8 g PEG 1000, and 54 g of water was then added, followed by removal from heat and continued stirring for another 10 minutes. As seen in previous experiments, protocols comprising emulsified pollen suspension solutions resulted in low seed set (Table 4).

TABLE 4

Seed set following airbrush application of corn pollen dried prior to suspension in oil

| Formulation | Ear 1 | Ear 2 | Ear 3 | Average |
|---|---|---|---|---|
| Dry, sprinkled | 140 | 133 | 126 | 133 ± 5.72 |
| 600 mg IL3 | 176 | 103 | 122 | 133.67 ± 30.92 |
| M3/PEG1000/METHOCEL ™ E19/Pluronic ® P104 | 11 | 15 | 12 | 12.67 ± 1.69 |

To determine whether varying the amount of Atlox™ LP-1 in pollen suspension solutions comprising Isopar M could improve seed set following pollination, the following oils were evaluated: 1) Isopar M; 2) 0.5% Atlox™ LP-1 in Isopar M; 3) 1.0% Atlox™ LP-1 in Isopar M; 4) IL3 (3.0% Atlox™ LP-1 in Isopar M). Pollen suspension solutions were created by adding 40 mg of fresh corn pollen to 400 mg of oil and 12 mg of Harborlite followed by vortexing. Pollen suspension solutions were stored at 4° C. for one hour to allow the polymeric dispersants to bind to the pollen surface, vortexed and then promptly sprayed over the ear using a Paasche TG-3F gravity-fed airbrush and a 0.66 mm tip at 30 psi. Ears were collected 13 days post pollination and evaluated for seed set. A higher seed set was achieved for all pollen suspension solutions comprising Atlox™ LP-1 compared Isopar M alone with solutions comprising 3.0% Atlox™ LP-1 performing best. (Table 5).

TABLE 5

Effect of surfactant concentration on seed set in oil-based pollen suspension solutions.

| Oil phase | Ear 1 | Ear 2 | Ear 3 | Average |
|---|---|---|---|---|
| Isopar M only | 6 | 11 | 10 | 9.0 ± 2.6 |
| 0.5% Atlox ™ LP-1 in Isopar M | 15 | 62 | 51 | 42.7 ± 24.6 |
| 1.0% Atlox ™ LP-1 in Isopar M | 42 | 42 | 47 | 43.7 ± 2.9 |
| 3.0% Atlox ™ LP-1 in Isopar M | 57 | 52 | 44 | 54.3 ± 2.5 |

Example 3. Liquid-Mediated Pollen Delivery in Corn Plants Using Aqueous Solutions Liquid-mediated delivery of monocot pollen to a female reproductive part of a recipient monocot plant is challenging as monocot pollen has a tendency to clump and lyse upon exposure to water. A liquid-mediated delivery method was developed to overcome these challenges and to deliver monocot pollen to a female reproductive part of a recipient monocot plant with minimal water using aqueous solutions.

A liquid-mediated pollen delivery method using reduced liquid phase was evaluated by examining seed set following pollination according to the following protocols: 1) 32 mg corn pollen, sprinkled; 2) 40 mg corn pollen+12 mg sieved Harborlite in 400 mg IL3; 3) 40 mg corn pollen+12 mg sieved Harborlite in 400 mg Isopar M; 4) 40 mg corn pollen+12 mg sieved Harborlite, 250 mg Isopar M added to vial and shaken immediately before spray; 5) 250 mg 1.0% Lutensol® XL-80 added to reservoir, 40 mg corn pollen+12 mg Harborlite added, sparged, and sprayed immediately; 6) 250 mg 1.0% Lutensol® XL-80 added to reservoir, 40 mg corn pollen+12 mg Harborlite added, sparged, and sprayed immediately at increased distance; 7) 400 mg of water added to reservoir, 40 mg corn pollen+12 mg Harborlite added, sparged, and sprayed immediately. Pollen suspension solutions were promptly sprayed over the ear using a Paasche TG-3F gravity-fed airbrush and a 0.66 mm tip at 30 psi. The IL3 pollen suspension solution produced a low seed set (Table 6). Protocols wherein dry pollen was briefly fluidized with either Isopar M or 1.0% Lutensol® XL-80 produced a very low seed set (Table 6). The protocol wherein the dry pollen was briefly fluidized in DI water produced an equivalent seed set to that produced using the IL3 pollen suspension solution despite poor fluidization of the pollen in water (Table 6).

TABLE 6

Seed set following airbrush application of pollen using reduced liquid phase.

| Protocol | Ear 1 | Ear 2 | Ear 3 | Average |
|---|---|---|---|---|
| Dry, sprinkled | 364 | 281 | — | 323 ± 59 |
| 400 mg IL3, vial | 52 | 25 | 54 | 44 ± 16 |
| 400 mg Isopar M, vial | 0 | 13 | 5 | 6 ± 7 |
| 250 mg Isopar M added to vial immediately before spray | 8 | 0 | 7 | 5 ± 4 |
| 250 mg 1.0% Lutensol ® XL-80, reservoir | 7 | 7 | 3 | 6 ± 2 |
| 250 mg 1.0% Lutensol ® XL-80, reservoir, increased distance | 0 | 0 | 0 | 0 |
| Water, reservoir | 82 | 20 | 66 | 56 ± 32 |

A liquid-mediated pollen delivery method using aqueous and oil phases was evaluated by examining seed set following pollination according to the following protocols: 1) 32 mg corn pollen, dry; 2) 40 mg corn pollen in 1.0% Pluronic® P104; 3) 40 mg corn pollen+12 mg sieved Harborlite+200 mg IL3 in 1.0% Pluronic® P104; 4) 40 mg corn pollen in 0.5% BREAK THRU® DA 647; 5) 40 mg corn pollen+12 mg sieved Harborlite+200 mg IL3 in 0.5% BREAK THRU® DA 647; 6) 40 mg corn pollen+12 mg sieved Harborlite+200 mg IL3 in 1.0% Poly Suga®Mulse; 7) 40 mg corn pollen+DI water; 8) 40 mg corn pollen+12 mg sieved Harborlite+200 mg IL3. Corn pollen was added either directly to 400 mg of the aqueous solution in a Paasche TG-3F gravity-fed airbrush reservoir or added as a suspension in oil. In the latter case, the corn pollen was added to vials containing IL3 and Harborlite and allowed to stand at 7° C. for 30 minutes prior to addition to 400 mg of the aqueous solution in the airbrush reservoir. The pollen suspension solution was sparged briefly prior to promptly spraying over the ear using either a 0.38 mm or 0.66 mm tip at either 20 or 30 psi. The ears were collected and evaluated 11 days post pollination (Table 7).

TABLE 7

Seed set following airbrush application of corn pollen using aqueous and oil phases.

| Protocol | Ear 1 | Ear 2 | Ear 3 | Average |
|---|---|---|---|---|
| Dry, sprinkled | 335 | 298 | 342 | 325 ± 24 |
| 1.0% Pluronic ® P104, 0.38 mm tip, 20 psi | 67 | 61 | 12 | 47 ± 30 |
| IL3/1.0% Pluronic ® P104, 0.38 mm, 20 psi | 10 | 12 | 13 | 12 ± 2 |
| 0.5% BREAK THRU ® DA 647, 0.38 mm, 20 psi | 73 | 103 | 0* | 88 ± 21 |
| IL3/0.5% BREAK THRU ® DA 647, 0.38 mm, 20 psi | 28 | — | 0 | 14 ± 20 |
| IL3/1.0% Poly Suga ®Mulse, 0.38 mm, 20 psi | 2 | 2 | 4 | 2.7 ± 1.5 |
| Water, 0.38 mm, 30 psi | 91 | 90 | 149 | 110 ± 34 |
| IL3, 0.66 mm, 30 psi | 63 | 97 | 57 | 72 ± 22 |

A liquid-mediated pollen delivery method using aqueous pollen suspension solutions was evaluated by examining seed set following pollination according to the following protocols: 1) 32 mg corn pollen, dry; 2) 40 mg corn pollen in 0.5% Pluronic® P104; 3) 40 mg corn pollen in 0.5% Calfax DB-45; 4) 40 mg corn pollen in 0.25% TOXIMUL® 8325; 5) 40 mg corn pollen in 0.25% Atlas G5000; 6) 40 mg corn pollen in 0.5% Surfynol®; 7) 40 mg corn pollen 0.5% METHOCEL™ F50; 8) 40 mg corn pollen in DI water. Corn pollen was added either directly to 400 mg of one of the aqueous solutions in the reservoir of a Paasche TG-3F gravity-fed airbrush or directly to a vial comprising the either water alone or the 0.5% Surfynol® solutions and vortexed. The pollen suspension solution was sparged briefly prior to promptly spraying over the ear using a 0.38 mm tip at either 20 or 30 psi. The ears were collected and evaluated 11 days post pollination (Table 8).

TABLE 8

Seed set following airbrush application of aqueous pollen suspension solutions.

| Protocol | Ear 1 | Ear 2 | Ear 3 | Average |
|---|---|---|---|---|
| Dry, sprinkled | 275 | 255 | 307 | 279 ± 22 |
| 0.5% Pluronic ® P104, 20 psi | 51 | 125 | 53 | 76 ± 42 |
| 0.5% Calfax DB-45, 20 psi | 0 | 0 | 0 | 0 |
| 0.25% TOXIMUL ® 8325, 20 psi | 88 | 63 | 67 | 73 ± 13 |
| 0.25% Atlas G5000, 20 psi | 54 | 52 | 4 | 37 ± 28 |
| 0.5% METHOCEL ™ F50, 20 psi | 194 | 122 | 124 | 147 ± 41 |
| 0.5% Surfynol ®, 30 psi | 0 | 0 | 6 | 2 ± 3 |
| DI water, 30 psi | 218 | 200 | 171 | 197 ± 24 |

A liquid-mediated pollen delivery method using vortexing prior to application was evaluated by examining seed set following pollination according to the following protocols: 1) 32 mg corn pollen, dry; 2) 40 mg corn pollen in DI water; 3) 40 mg corn pollen in 0.5% METHOCEL™ F50; 4) 40 mg corn pollen in 1.0% METHOCEL™ E19; 5) 40 mg corn pollen in 0.5% Break-thru DA 675. Corn pollen was added to 400 mg of aqueous solution in a vial, vortexed, promptly transferred to the reservoir of a Paasche TG-3F gravity-fed airbrush, and sprayed over ears using the airbrush and a 0.38 mm tip at 30 psi. The ears were collected and evaluated 11 days post pollination (Table 9).

TABLE 9

Seed set following airbrush application of aqueous pollen suspension solutions with brief vortexing prior to application.

| Protocol | Ear 1 | Ear 2 | Ear 3 | Average |
|---|---|---|---|---|
| Dry, sprinkled | 373 | 392 | 367 | 377 ± 13 |
| DI water | 21 | 17 | 49 | 29 ± 17 |
| 0.5% METHOCEL ™ F50 | 133 | 3 | 66 | 67 ± 65 |
| 1.0% METHOCEL ™ E19 | 6 | 28 | 35 | 23 ± 15 |
| 0.5% Break-thru DA 675 | 13 | 14 | 29 | 19 ± 9 |

A liquid-mediated pollen delivery method using dilute, aqueous pollen suspension solutions was evaluated by examining seed set following pollination according to the following protocols: 1) 32 mg corn pollen, dry; 2) 40 mg corn pollen in 0.5% METHOCEL™ F50; 3) 40 mg corn pollen in 0.5% METHOCEL™ E19; 4) 40 mg corn pollen in Break-thru DA 675; 5) 40 mg corn pollen in 0.2% Atlox™ 4915; 6) 40 mg corn pollen in 0.2% TOXIMUL® 8320; 7) 40 mg corn pollen in 0.2% TOXIMUL® 8242; 8) 40 mg pollen in DI water. Aqueous solution (400 mg) was added to a vial containing corn pollen, vortexed, transferred to the reservoir of a Paasche TG-3F gravity-fed airbrush, sparged, and sprayed promptly over the ear using a 0.38 mm tip at 30 psi. The ears were collected and evaluated 11 days post pollination (Table 10).

TABLE 10

Seed set following airbrush application of dilute, aqueous pollen suspension solutions.

| Protocol | Ear 1 | Ear 2 | Ear 3 | Average |
|---|---|---|---|---|
| Dry, sprinkled | 287 | 378 | 340 | 335 ± 46 |
| 0.5% METHOCEL ™ F50 | 0* | 20* | 27* | 16 ± 14 |
| 0.5% METHOCEL ™ E19 | 61 | 65 | 82 | 69 ± 11 |
| 0.5% Break-thru DA 675 | 36 | 24† | 77 | 32 ± 6 |
| 0.2% Atlox ™ 4915 | 48 | 57 | 84 | 63 ± 18 |
| 0.2% TOXIMUL ® 8320 | 40 | 28 | 228 | 99 ± 112 |
| 0.2% TOXIMUL ® 8242 | 12 | 36 | 14 | 21 ± 13 |
| DI Water | 197 | 51 | 7 | 85 ± 99 |

A liquid-mediated pollen delivery method using variable pollen loads was evaluated by examining seed set following pollination according to the following protocols: 1) 32 mg corn pollen, dry 2) 40 mg corn pollen in 400 mg 0.5% METHOCEL™ E19; 3) 40 mg corn pollen in 800 mg 0.5% METHOCEL™ E19; 4) 80 mg corn pollen in 800 mg 0.5% METHOCEL™ E19; 5) 40 mg corn pollen in 400 mg 0.2% TOXIMUL® 8320; 6) 40 mg corn pollen in 800 mg 0.2% TOXIMUL® 8320; 7) 80 mg corn pollen in 800 mg 0.2% TOXIMUL® 8320. Corn pollen was added to aqueous solution in a vial, vortexed, promptly transferred to the reservoir of a Paasche TG-3F gravity-fed airbrush, sparged, and promptly sprayed over ears using the airbrush and a 0.38 mm tip at 30 psi. The ears were collected and evaluated 11 days post pollination (Table 11).

TABLE 11

Seed set following airbrush application of aqueous pollen suspension solutions with variable pollen loads.

| Protocol | Ear 1 | Ear 2 | Ear 3 | Average |
|---|---|---|---|---|
| Dry, sprinkled | 274 | 210 | 307 | 264 ± 49 |
| 40 mg pollen in 400 mg 0.5% METHOCEL ™ E19 | 25 | 75 | — | 50 ± 35 |

TABLE 11-continued

Seed set following airbrush application of aqueous pollen suspension solutions with variable pollen loads.

| Protocol | Ear 1 | Ear 2 | Ear 3 | Average |
|---|---|---|---|---|
| 40 mg pollen in 800 mg 0.5% METHOCEL ™ E19 | 30 | 19 | — | 25 ± 8 |
| 80 mg pollen in 800 mg 0.5% METHOCEL ™ E19 | 119 | 31 | 10 | 53 ± 57 |
| 40 mg pollen in 400 mg 0.2% TOXIMUL ® 8320 | †30 | 87 | 88 | 88 ± 1 |
| 40 mg pollen in 800 mg 0.2% TOXIMUL ® 8320 | 36 | 59 | 58 | 51 ± 13 |
| 80 mg pollen in 800 mg 0.2% TOXIMUL ® 8320 | 27 | 24 | *13 | 26 ± 2 |

*Some of the pollen suspension was dumped on the ear.
†Malformed ear fused with stalk A liquid-mediated pollen delivery method using multiple airbrush applications was evaluated by examining seed set following pollination according to the following protocols: 1) 32 mg corn pollen, dry 2) 40 mg corn pollen in 400 mg DI water; 3) 40 mg corn pollen in 400 mg DI water, 3 applications over 3 days; 4) 120 mg corn pollen in 1200 mg DI water; 5) 40 mg corn pollen in 400 mg 0.5% METHOCEL™ F50; 6) 40 mg corn pollen in in 400 mg 0.5% METHOCEL™ F50, 3 applications over 3 days; 7) 120 mg corn pollen in 1200 mg 0.5% METHOCEL™ F50; 8) 40 mg corn pollen in 400 mg 0.2% TOXIMUL® 8320; 9) 40 mg pollen 400 mg 0.2% TOXIMUL® 8242. Corn pollen was added to the aqueous solution in the reservoir of a Paasche TG-3F gravity-fed airbrush, sparged, and promptly sprayed over the ear using a 0.38 mm tip at 30 psi or 40 psi (protocol 4 only). No vortexing was used. The ears were collected and evaluated 10 days post pollination. Full seed set was achieved with the pollen suspension solution comprising 40 mg pollen in 400 mg DI water when applied to corn silks for three consecutive days (Table 12).

TABLE 12

Seed set following multiple airbrush applications of aqueous pollen suspension solutions over consecutive days with variable pollen load.

| Protocol | Ear 1 | Ear 2 | Ear 3 | Average |
|---|---|---|---|---|
| Dry, sprinkled | 276 | 207 | 276 | 253 ± 40 |
| 40 mg pollen in 400 mg DI, 1× | 41 | 4 | 43 | 29 ± 22 |
| 40 mg pollen in 400 mg DI, 3× | 269 | 257 | 358 | 295 ± 55 |
| 120 mg pollen in 1200 mg DI | 60 | 50 | 75 | 62 ± 15 |
| 40 mg pollen in 400 mg 0.5% METHOCEL ™ F50, 1× | 80 | 100 | 50 | 77 ± 25 |
| 40 mg pollen in 400 mg 0.5% METHOCEL ™ F50, 3× | 208 | 273 | 120 | 200 ± 77 |
| 120 mg pollen in 1200 mg 0.5% METHOCEL ™ F50 | 72 | 47 | 55 | 58 ± 15 |
| 40 mg pollen in 400 mg 0.2% TOXIMUL ® 8320 | 87 | 89 | 76 | 84 ± 7 |
| 40 mg pollen in 400 mg 0.2% TOXIMUL ® 8242 | 79 | 18 | 41 | 46 ± 31 |

A liquid-mediated pollen delivery method using multiple applications of aqueous pollen suspension solutions and variable agitation methods was evaluated by examining seed set following pollination according to the following protocols: 1) 32 mg corn pollen, dry; 2) 40 mg corn pollen in tap water, sparge; 3) 40 mg corn pollen in tap water, vortex; 4) 40 mg corn pollen in 0.5% METHOCEL™ F50, sparge; 5) 40 mg corn pollen in 0.5% METHOCEL™ F50, vortex; 6) 40 mg corn pollen in 0.2% TOXIMUL® 8320, sparge; 7) 40 mg corn pollen in 0.2% TOXIMUL® 8320, vortex; 8) 40 mg corn pollen in 0.2% Atlox™ 4915, sparge. Corn pollen was added to the aqueous solution in either a vial and vortexed or in the reservoir of a Paasche TG-3F gravity-fed airbrush, and sparged immediately prior to spraying promptly over the ear using a 0.38 mm tip at 30 psi. All liquid-mediated delivery protocols were repeated for a total of three applications on three consecutive days. The ears were collected and evaluated 10 days after the first pollination. The three vortexed pollen suspension solutions produced ears that were visually full or nearly full (Table 13).

TABLE 13

Seed set following multiple airbrush applications of aqueous pollen suspension solutions over consecutive days using variable agitation methods.

| Protocol | Ear 1 | Ear 2 | Ear 3 | Average |
|---|---|---|---|---|
| Dry, sprinkled | 456 | 416 | 498 | 457 ± 41 |
| Tap water, sparge | 62 | 179 | 203 | 148 ± 75 |
| 0.5% METHOCEL ™ F50, sparge | 101 | 130 | 73 | 101 ± 28 |
| 0.2% TOXIMUL ® 8320, sparge | 199 | 169 | 131 | 166 ± 34 |
| 0.2% Atlox ™ 4915, sparge | 166 | 160 | — | 163 ± 4 |
| Tap water, vortex | 372 | 300 | 407 | 360 ± 55 |
| 0.5% METHOCEL ™ F50, vortex | 260 | 353 | 315 | 309 ± 47 |
| 0.2% TOXIMUL ® 8320, vortex | 294 | 277 | 346 | 306 ± 36 |

A liquid-mediated pollen delivery method using aqueous pollen suspensions over several days was evaluated by examining seed set following pollination according to the following protocols: 1) 32 mg corn pollen dry; 2) 40 mg corn pollen in 400 mg tap water, Day 1 only; 3) 40 mg corn pollen in 800 mg tap water, Day 1 only; 4) 40 mg corn pollen in 400 mg tap water, Days 1 and 2; 5) 40 mg corn pollen in 400 mg tap water, Day 1+40 mg corn pollen in 400 mg 0.5% METHOCEL™ F50, Day 2; 6) 40 mg corn pollen in 400 mg tap water, Day 1+40 mg corn pollen in 400 mg 0.2% Atlox™ 4915, Day 2; 7) 40 mg corn pollen in 400 mg 0.5% METHOCEL™ F50, Days 1 and 2; 8) 40 mg corn pollen in 400 mg 0.2% Atlox™ 4915, Day 1 only; 9) 20 mg in 400 mg tap water, Day 1 only. Corn pollen was added to the aqueous solution in the reservoir of a Paasche TG-3F gravity-fed airbrush and sparged immediately prior to spraying promptly over the ear using a 0.38 mm tip at 30 psi. On day 1, ear 3 of protocol 7 was pollinated by adding the aqueous phase to the pollen vial, vortexing, transferring to the airbrush and sparging immediately prior to spraying promptly over the ear using a 0.38 mm tip at 30 psi. The ears were collected and evaluated 10 days after the first pollination. All protocols in which pollinations were repeated on two consecutive days produced a higher seed set compared to one day pollination protocols (Table 14).

TABLE 14

Seed set following airbrush application of aqueous pollen suspension solutions over consecutive days.

| Protocol | Ear 1 | Ear 2 | Ear 3 | Average |
|---|---|---|---|---|
| Dry, sprinkled | 463 | 446 | 460 | 456 ± 9 |
| 400 mg tap water, 1× | 30 | 202 | 174 | 135 ± 92 |
| 800 mg tap water, 1× | 83 | 182 | 62 | 109 ± 64 |
| 400 mg tap water, 2× | 174 | 136 | 122 | 144 ± 27 |
| Tap water (Day 1)/0.5% METHOCEL ™ F50 (Day 2) | 142 | 210 | 217 | 190 ± 41 |
| Tap water (Day 1)/0.2% Atlox ™ 4915 (Day 2) | 236 | 200 | 163 | 200 ± 37 |
| 400 mg 0.5% METHOCEL ™ | 186 | 207 | 339 | 244 ± 83 |

TABLE 14-continued

Seed set following airbrush application of aqueous pollen suspension solutions over consecutive days.

| Protocol | Ear 1 | Ear 2 | Ear 3 | Average |
|---|---|---|---|---|
| F50, 2× | | | | |
| 400 mg 0.2% Atlox ™ 4915, 1× | 33 | 24 | 107 | 55 ± 46 |
| 20 mg corn pollen in 400 mg tap water, 1× | 18 | 38 | 24 | 27 ± 10 |

A liquid-mediated pollen delivery method using aqueous pollen suspensions was evaluated by examining seed set following pollination according to the following protocols: 1) 32 mg corn pollen dry; 2) 32 mg corn pollen in 0.2% METHOCEL™ F50; 3) 32 mg corn pollen in 10% sucrose (weight/volume); 4) 32 mg corn pollen in 20% sucrose (weight volume); 5) 32 mg corn pollen in 30% sucrose (weight/volume); and 6) 32 mg corn pollen in 40% sucrose (weight/volume). The pollen suspension solutions were sprayed over the ear using a Paasche TG-3F gravity-fed airbrush. All pollinations were repeated on two consecutive days. Pollinations with aqueous solutions comprising 10%, 20%, 30%, and 40% sucrose produced a high seed set. (Table 15).

TABLE 15

| Seed set following airbrush application of aqueous pollen suspension solutions comprising sucrose. | |
|---|---|
| Protocol | Average |
| Dry, sprinkled | 386 |
| 0.2% METHOCEL ™ F50 | 154 |
| 10% Sucrose (weight/volume) | 257 |
| 20% Sucrose (weight/volume) | 208 |
| 30% Sucrose (weight/volume) | 147 |
| 40% Sucrose (weight/volume) | 156 |

A liquid-mediated pollen delivery method using aqueous pollen suspensions containing non-phytotoxic solutes to reduce water activity was evaluated by examining seed set following pollination according to the following protocols: 1) 32 mg corn pollen dry, sprinkled; 2) 32 mg corn pollen in 0.2% METHOCEL™ F50; 3) 32 mg corn pollen in 0.5% Poly SugaMulse D6; 4) 32 mg corn pollen in 0.2% METHOCEL™ F50+20% maltose monohydrate; 5) 32 mg corn pollen in 0.5% Poly SugaMulse D6+20% maltose monohydrate; 6) 32 mg corn pollen in 0.2% METHOCEL™ F50+10% sucrose; 7) 32 mg corn pollen in 0.5% Poly SugaMulse D6+10% sucrose; 8) 32 mg corn pollen in 0.2% METHOCEL™ F50+10% glycerol ethoxylate; and 9) 32 mg corn pollen in 0.2% METHOCEL™ F50+20% glycerol ethoxylate. Three ears, all four days past the beginning of silking, were sprayed with a suspension of 32 mg of fresh pollen in 320 μl of aqueous phase using an airbrush at 30 psi. All pollinations were repeated on two consecutive days. Pollinations with aqueous solutions comprising 10% glycerol ethoxylate, 10% sucrose, and 20% maltose monohydrate produced significantly higher seed set compared to aqueous solutions, which did not comprise a solute to reduce water activity (0.2% METHOCEL™ F50 alone) (Table 16).

TABLE 16

| Seed set following airbrush application of aqueous pollen suspension solutions comprising maltose, sucrose, or glycerol ethoxylate. | | | | |
|---|---|---|---|---|
| Protocol | Ear 1 | Ear 2 | Ear 3 | Average |
| Dry, sprinkled | 381 | 311 | 319 | 337 ± 38 |
| 0.2% METHOCEL ™ F50 | 82 | 68 | 41 | 64 ± 21 |
| 0.2% METHOCEL ™ F50 + 20% maltose | 84 | 171 | 19 | 91 ± 76 |
| 0.5% PS Mulse + 10% maltose | 55 | 116 | 160 | 110 ± 53 |
| 0.5% PS Mulse + 20% maltose | 122 | 89 | 156 | 122 ± 34 |
| 0.2% METHOCEL ™ F50 + 10% sucrose | 69 | 14 | 16 | 33 ± 31 |
| 0.5% PS Mulse + 10% sucrose | 202 | 226 | 154 | 194 ± 37 |
| 0.2% METHOCEL ™ F50 + 10% glycerol ethoxylate | 33 | 122 | 192 | 116 ± 80 |
| 0.2% METHOCEL ™ F50 + 20% glycerol ethoxylate | 20 | 39 | 9 | 23 ± 15 |

Example 4. Liquid-Mediated Pollen Delivery to Corn Plants in Field and Greenhouse Conditions A suitable liquid-mediated pollen delivery method was evaluated by examining seed set following pollination according to the following protocol. Corn pollen was mechanically collected from inbred male plants and stored in a cooler for several hours prior to production of a pollen suspension solution comprising 7.5 g of corn pollen and 68 ml of 0.2% METHOCEL™ F50. The solution was shaken and poured into the reservoir of a Paasche™ LMR-1 airgun with a gravity-feed reservoir, and sprayed while walking at 3 mph along one side of a 50-foot row of cytoplasmic male-sterile corn plants, which were spaced 6 feet apart. Three passes were made along each side of the row, corresponding to delivery of 150 mg pollen per plant. The liquid-mediated delivery protocol was repeated for a total of three applications on three consecutive days, resulting in total pollen delivery of 450 mg pollen per plant in each trial. Two trials using two different cytoplasmic male-sterile corn lines as the pollen recipient were completed using the above referenced protocol, and despite high fungal and insect pressure, seed sets of 76±44 and 156±60 kernels per ear were achieved. The typical seed set for the corn variety used in this trial is approximately 300 kernels per ear. Negative control plants produced only one seed per ear on average, demonstrating the near-perfect male sterility of the variety used in these trials.

A suitable liquid-mediated pollen delivery method was evaluated by examining seed set following pollination according to the following protocol. A row of six female plants were pollinated in a greenhouse using a pollen suspension solution comprising 10% corn pollen in 0.2% METHOCEL™ F50 and a Graco® EFX automatic airgun with an atomization air pressure of 5 psi. The six plants were sprayed in a continuous back-and-forth pass with the airgun using a feed of 10% pollen in 0.2% METHOCEL™ F50 pumped to the airgun at rate of 15 ml/min with a peristaltic pump. This produces a well-atomized, well-targeted spray at a comparatively low velocity, which improves pollen retention on the ears. In this trial the liquid-mediated delivery protocol was performed on only one day, but still produced a seed set of 201±117 kernels per ear. The typical seed set for the corn variety used in this trial is approximately 300 kernels per ear. This demonstrates that good seed set can be achieved with minimal pollen by means of well-directed, gentle air-assisted spraying of pollen in an aqueous medium.

A suitable liquid-mediated pollen delivery method was evaluated by examining seed set following pollination according to the following protocol. A row of five female plants were pollinated using a pollen suspension solution comprising 10% corn pollen in 0.2% METHOCEL™ F50 and a stainless steel Teejet® TP 6501 nozzle. This nozzle produces a particularly fine spray as a narrow 65-degree fan that can be accurately targeted. The solution was pumped at 270 ml/min through the nozzle, which was passed back and forth over the row of five plants for 5 seconds, resulting in the delivery of 450 mg pollen/plant. The protocol was repeated for a total of three applications on three consecutive days, and resulted in a seed set of 177±40 kernels per ear. This demonstrates that acceptable seed set can be achieved with conventional nozzles that produce a very fine spray.

Example 5. Further Applications of the Novel Liquid-Mediated Pollen Delivery Method Transgenic seeds or gene-edited seeds of recipient plants may be directly generated through liquid-mediated pollination with exogenous DNA-transformed pollen. Collected pollen may be transformed through physical methods such as electroporation, bombardment and sonication, *Agrobacterium* infection, pollen tube-mediated transfection, or magnetofection (Zhao, et al., 2017). For example, CRISPR/Cpf1 reagents may be delivered into purified pollen grains using electroporation or magnetofection. The transformed pollen is then selected and placed into a liquid solution provided herein. The pollen solution may then be sprayed onto the female reproductive portion of a recipient plant to create genome-edited seeds. It is feasible to utilize the liquid-mediated pollination methods provided herein and CRISPR/Cpf1-based gene editing for trait discovery and improvement in plants. This combination obviates the need for the laborious steps of tissue culture while producing transgenic or gene-edited plants from transformed seeds within a short period of time.

What is claimed is:

1. A pollen suspension solution comprising:
   a) an isoparaffin oil, about 2% to about 20% monocot pollen by weight, and a surfactant present in an amount equal to or less than about 3.0% by weight; or
   b) an aqueous solution, about 2% to about 20% monocot pollen by weight, and a surfactant present in an amount of less than about 1.0% by weight, wherein the surfactant is selected from the group consisting of a modified cellulose polymer and a block copolymer of ethylene oxide and propylene oxide;
wherein said pollen suspension solution is capable of producing a substantially equivalent number of seeds when sprayed onto at least a first female reproductive part of a recipient monocot plant compared to the number of seeds produced using a conventional pollination technique.

2. The pollen suspension solution of claim 1, wherein the pollen suspension solution comprises from about 2% to about 15% monocot pollen by weight.

3. The pollen suspension solution of claim 1, wherein the pollen suspension solution comprises an isoparaffin oil, about 2% to about 20% monocot pollen by weight, a surfactant present in an amount equal to or less than about 3.0% by weight, and an aqueous solution.

4. The pollen suspension solution of claim 1, wherein said pollen suspension solution comprises an aqueous solution, about 2% to about 20% monocot pollen by weight, and a surfactant present in an amount of less than about 1.0% by weight, wherein the surfactant is selected from the group consisting of a modified cellulose polymer and a block copolymer of ethylene oxide and propylene oxide.

5. The pollen suspension solution of claim 1, wherein the pollen suspension solution comprises less than about 1.0% surfactant by weight.

6. The pollen suspension solution of claim 4, wherein said surfactant is a block copolymer of ethylene oxide and propylene oxide.

7. The pollen suspension solution of claim 6, wherein said block copolymer of ethylene oxide and propylene oxide further comprises a terminal alkyl group.

8. The pollen suspension solution of claim 4, wherein said surfactant is a modified cellulose polymer.

9. The pollen suspension solution of claim 4, wherein said pollen suspension solution comprises an isoparaffin oil, about 2% to about 20% monocot pollen by weight, and a surfactant present in an amount equal to or less than about 3.0% by weight.

10. A method for liquid-mediated delivery of pollen to a female reproductive part of a recipient monocot plant comprising the steps of:
    a) obtaining the pollen suspension solution of claim 1; and
    b) spraying said pollen suspension solution onto at least a first female reproductive part of the recipient monocot plant, thereby pollinating the female reproductive part with the pollen.

11. The method of claim 10, wherein the recipient monocot plant is a) selected from the group consisting of a corn plant, a wheat plant, and a rice plant; or b) male sterile at the time of said pollinating.

12. The method of claim 10, further comprising repeating said steps a), and b) on two or more consecutive days.

13. The method of claim 10, wherein a) the recipient monocot plant is genetically male sterile; b) the recipient monocot plant is treated with a gametocide; or c) the male reproductive parts or parts thereof of the recipient monocot plant have been removed.

14. The method of claim 10, wherein said pollen suspension solution comprises an aqueous solution, about 2% to about 20% monocot pollen by weight, and less than about 1.0% surfactant by weight, wherein the surfactant is selected from the group consisting of a modified cellulose polymer and a block copolymer of ethylene oxide and propylene oxide.

15. The method of claim 14, wherein said surfactant is a block copolymer of ethylene oxide and propylene oxide.

16. The method of claim 15, wherein said block copolymer of ethylene oxide and propylene oxide further comprises a terminal alkyl group.

17. The method of claim 14, wherein said surfactant is a modified cellulose polymer.

18. The method of claim 10, wherein said pollen suspension solution comprises an isoparaffin oil, about 2% to about 20% monocot pollen by weight, and a surfactant present in an amount equal to or less than about 3.0% by weight.

19. The method of claim 10, wherein said pollen suspension solution comprises from about 2% to about 15% pollen by weight.

20. The method of claim 10, wherein said liquid pollen suspension is produced less than about 20 minutes prior, less than about 5 minutes prior, or less than about 30 seconds prior to said spraying.

21. The method of claim 10, wherein said method produces a substantially equivalent number of seeds compared to the number of seeds produced using a conventional pollination technique.

22. The method of claim 10, wherein a) said spraying comprises air-assisted spraying; or b) said liquid pollen suspension is produced using agitation of said pollen suspension solution.

23. The method of claim 22, wherein a) said spraying produces droplets with a volume weighted mean droplet diameter of less than about 300 μM; b) liquid cannot be observed visually at a distance of about 36 inches from the female reproductive part of the recipient monocot plant following said air-assisted spraying; or c) said agitation comprises vortexing or sparging said pollen suspension solution.

24. The method of claim 10, further comprising collecting seed resulting from said pollinating.

25. The method of claim 24, further comprising crossing a progeny plant grown from said seed with itself or a second plant.

26. The method of claim 10, the method further comprising the steps of:
 c) harvesting seed produced from said pollination; and
 d) identifying hybrid progeny.

27. The pollen suspension solution of claim 1, wherein said pollen suspension solution further comprises at least one solute at a concentration of about 0.5M to about 3.0M to increase the tonicity of the solution, wherein said solute is impermeable to said pollen in said solution.

28. The pollen suspension solution of claim 27, wherein the solute is selected from the group consisting of a monosaccharide, a disaccharide, a polysaccharide, a polyhydric alcohol, a polyethylene glycol solute, glucose, fructose, galactose, sucrose, lactose, maltose rehalose, cellobiose, chitobiose, kojibiose, nigerose, isomaltose, trehalose, sophorose, laminaribiose, gentiobiose, trehalulose, turanose, maltulose, leucrose, isomaltulose, gentiobiulose, mannobiose, melibiose, melibiulose, rutinose, rutinulose, xylobiose, maltotriose, melezitose, nigerotriose, maltotriulose, raffinose, kestose, maltodextrin, starch, glycogen, galactogen, cellulose, chitin, pectin, peptidoglycan, mannitol, sorbitol, xylitol, lactitol, isomalt, maltitol, sodium chloride, polyethylene glycol, and glycerol ethoxylate.

29. The pollen suspension solution of claim 27, wherein the solute is present in the solution at a) a concentration of between about 0.5M and about 3.0M; or b) about 5% to about 50% solute (weight/volume).

30. A method for liquid-mediated delivery of pollen to a female reproductive part of a recipient monocot plant comprising the steps of:
 a) obtaining the pollen suspension solution according to claim 27; and
 b) spraying said pollen suspension solution onto at least a first female reproductive part of the recipient monocot plant, thereby pollinating the female reproductive part with the pollen.

31. The method of claim 30, wherein said liquid pollen suspension solution is produced less than about 6 hours or less than about 30 minutes prior to said spraying.

32. The pollen suspension solution of claim 1, wherein the monocot pollen is selected from the group consisting of corn pollen, wheat pollen, and rice pollen.

* * * * *